United States Patent [19]
Judge

[11] Patent Number: 6,079,217
[45] Date of Patent: *Jun. 27, 2000

[54] METHOD AND SYSTEM FOR THE DETERMINATION OF A TERNARY REFRIGERANT MIXTURE COMPOSITION

[75] Inventor: John F. Judge, Stewartstown, Pa.

[73] Assignee: York International Corporation, York, Pa.

[*] Notice: This patent issued on a continued prosecution application filed under 37 CFR 1.53(d), and is subject to the twenty year patent term provisions of 35 U.S.C. 154(a)(2).

[21] Appl. No.: 09/127,986

[22] Filed: Aug. 3, 1998

[51] Int. Cl.$^7$ .................................................. G01K 13/00
[52] U.S. Cl. .................... 62/129; 62/149; 62/127; 62/77; 62/102; 62/114; 62/502
[58] Field of Search ............................... 62/149, 129, 77, 62/102, 114, 502, 127

[56] References Cited

U.S. PATENT DOCUMENTS

| | | | |
|---|---|---|---|
| 5,363,662 | 11/1994 | Todack | 62/85 |
| 5,377,493 | 1/1995 | Friedland | 62/149 |
| 5,560,213 | 10/1996 | Wieszt | 62/125 |
| 5,606,862 | 3/1997 | Peckjian et al. | 62/149 |
| 5,626,026 | 5/1997 | Sumida et al. | 62/129 |
| 5,647,222 | 7/1997 | Sarakinis | 62/129 |
| 5,678,415 | 10/1997 | Peckjian et al. | 62/149 |
| 5,722,247 | 3/1998 | Albertson et al. | 62/149 |
| 5,758,506 | 6/1998 | Hancock et al. | 62/149 |

FOREIGN PATENT DOCUMENTS

| | | | |
|---|---|---|---|
| 0 750 166 | 12/1996 | European Pat. Off. | F25B 13/00 |
| 08-261576 | 10/1996 | Japan | F25B 1/00 |
| 10-068555 | 3/1998 | Japan | F25B 1/00 |

OTHER PUBLICATIONS

PCT Search Report for PCT/US99/17466, Oct. 29, 1999.
WPI Abstract of JP 10 06855A, WPI Acc. No. 98–225737/199820 (1998).
WPI Abstract of JP 08 261576A, WPI Acc. No. 96–508740/199651 (1996).

Primary Examiner—Henry Bennett
Assistant Examiner—Mark Shulman
Attorney, Agent, or Firm—Finnegan, Henderson, Farabow, Garrett & Dunner, L.L.P.

[57] ABSTRACT

A method for determining the composition of a ternary refrigerant in a refrigeration system. The method calculates the composition of the ternary refrigerant under the assumption that the expansion cycle is isenthalpic and that the ratio of two components in the ternary mixture remain fixed in relation to one another before and after the expansion. These assumptions permit the calculation of composition of a ternary mixture with relatively few inputs.

9 Claims, 1 Drawing Sheet

METHOD AND SYSTEM FOR THE DETERMINATION OF A TERNARY REFRIGERANT MIXTURE COMPOSITION

II. BACKGROUND OF THE INVENTION

A. Field of the Invention

The present invention relates to refrigeration or air conditioning systems using a ternary refrigerant and having a cycle comprising an expander which expands the refrigerant from a liquid phase to a liquid phase and vapor phase. Specifically, the present invention provides a method and system for determining the composition of a ternary refrigerant in a novel and elegant manner.

Chlorofluorocarbon refrigerants, such as dichlorodifluoromethane ("R-22"), present a threat to the earth's ozone layer. Accordingly, practitioners in the air conditioning and refrigeration art have long sought refrigerant compositions which are as effective as chlorofluorocarbon refrigerants, but which are also safe for use in the environment. This search has led to the development of ternary refrigerants, such as "R-407C", a ternary mixture of difluoromethane ("R-32"), pentafluorethane ("R-125") and 1,1,1,2-tetrafluoroethane ("R-134a") combined in a weight ratio of 23/25/52, with properties similar to R-22. The abbreviations R-407C, R-134a, R-125, R-32, R-22, and many others, are designated by the American Society of Heating, Refrigeration and Air Conditioning Engineers (ASHRAE) and are used throughout the industry and in the present disclosure.

The use of ternary refrigerants poses certain problems. Refrigeration systems periodically leak, which may cause fractionation, and a consequent change in composition of the refrigerant. One problem posed by the use of ternary refrigerants has been the inability to determine whether and the degree to which a ternary refrigerant has fractionated.

Measuring the composition of a ternary refrigerant, such as R-407C, is more complex than measuring the composition of a binary refrigerant because each component adds a degree of freedom to the thermodynamic equation of state, requiring the input of more process variables to reach a solution. A simple method of determining the composition of a ternary refrigerant would greatly facilitate the use and application of new ternary refrigerants.

B. Description of the Prior Art

Methods are known wherein thermodynamic properties are measured, and equations of state are used to calculate the composition of a refrigerant. For example, U.S. Pat. No. 5,626,026 to Sumida describes a complex process for control of a refrigeration system. Sumida describes a system to calculate the composition of a refrigerant, to control the compressor and expansion valve in a refrigeration system. However, the process described in the Sumida is not directly applicable to ternary refrigerants.

III. SUMMARY OF THE INVENTION

The objects of the invention are to provide an elegant and simple method and system for determining the composition of a ternary refrigerant in an operating refrigeration system, and a system for carrying out the method.

The method for determining the composition of a ternary refrigerant in a refrigeration system having an expansion device, comprises: providing a ternary refrigerant, having a first component, a second component, and a third component, in a refrigerant loop including an expansion device; measuring an upstream temperature of the ternary refrigerant in the liquid phase upstream of the expansion device; expanding the refrigerant in the expansion device so that the ternary refrigerant is present in a vapor and liquid phase downstream of the expansion device; measuring a downstream temperature and a downstream pressure of the ternary refrigerant downstream of the expansion device; and calculating the composition of the ternary refrigerant with a thermodynamic equation of state, wherein the step of calculating assumes that the enthalpy is a function of temperature alone and a constant ratio of the first component to the second component in the liquid phase upstream of the expansion device and in the liquid and the vapor phase downstream of the expansion device.

The system for determining the composition of a ternary refrigerant in a refrigeration loop comprises: an expansion device, flow connected in the refrigeration loop, adapted to expand a ternary refrigerant from a liquid phase to a liquid phase and a vapor phase; a first temperature sensing device disposed to measure the temperature of the ternary refrigerant mixture in the liquid phase upstream of the expansion device; a second temperature measuring device and a pressure sensing device disposed to measure the temperature and pressure, respectively, of the ternary refrigerant in the vapor phase and the liquid phase downstream of the expansion device, and a calculator that receives input from the first temperature measuring device, the second temperature measuring device, and the pressure measuring device, and no input from other process variables, and calculates the composition of the ternary refrigerant, based on the assumption that the enthalpy is a function of temperature alone and that at least two components of the ternary refrigerant maintain a constant ratio of a first component to a second component in the liquid phase upstream of the expansion device and in the liquid and the vapor phase downstream of the expansion device.

As explained in more detail below, the methods and systems of the present invention are particularly useful in determining the composition of refrigerants in systems initially charged with R-407C and similar ternary refrigerants. Once the composition is calculated, this calculated value can be used for a variety of purposes, including system control or recharging procedures.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

IV. BRIEF DESCRIPTION OF THE DRAWINGS

V. DESCRIPTION OF THE PREFERRED EMBODIMENT(S)

Figure 1:
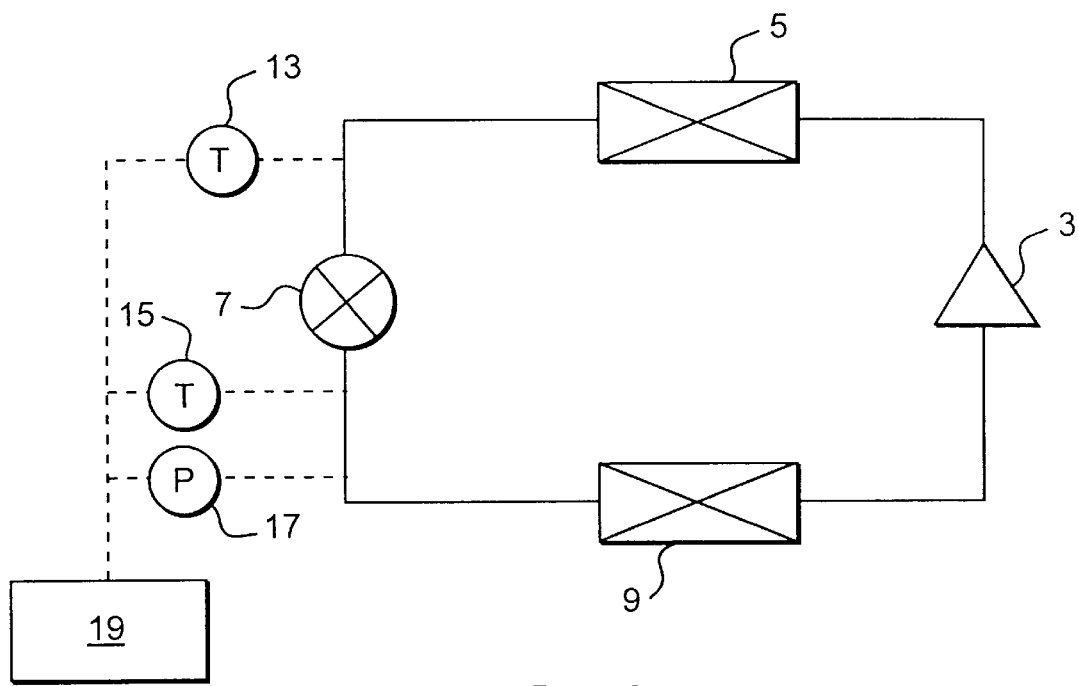
FIG. 1 is a schematic view of a refrigeration system.

FIG. 1 depicts an exemplary refrigeration system or loop comprising a compressor 3, condenser 5, expansion device (sometimes hereinafter referred to as "expansion valve") 7, and evaporator 9. The measurement devices on the refrigeration system include a first temperature measuring device or sensor 13, a second temperature measuring device or sensor 15, and a pressure measuring device or sensor 17. In the preferred embodiment, the measurement devices provide the only required process variable inputs to a calculator 19, such as a microprocessor. Alternatively, a family of charts, tables or graphs may be used to calculate the ternary refrigerant composition from the above process variable inputs.

The compressor 3, condenser 5, expansion device 7, and evaporator 9 are connected in a loop by piping as shown in FIG. 1. Other elements may be added to the refrigeration system as would be evident to one of ordinary skill in the art. For example, an accumulator may be placed upstream of the compressor to control the quality of the feed to the compressor.

Figure 2:
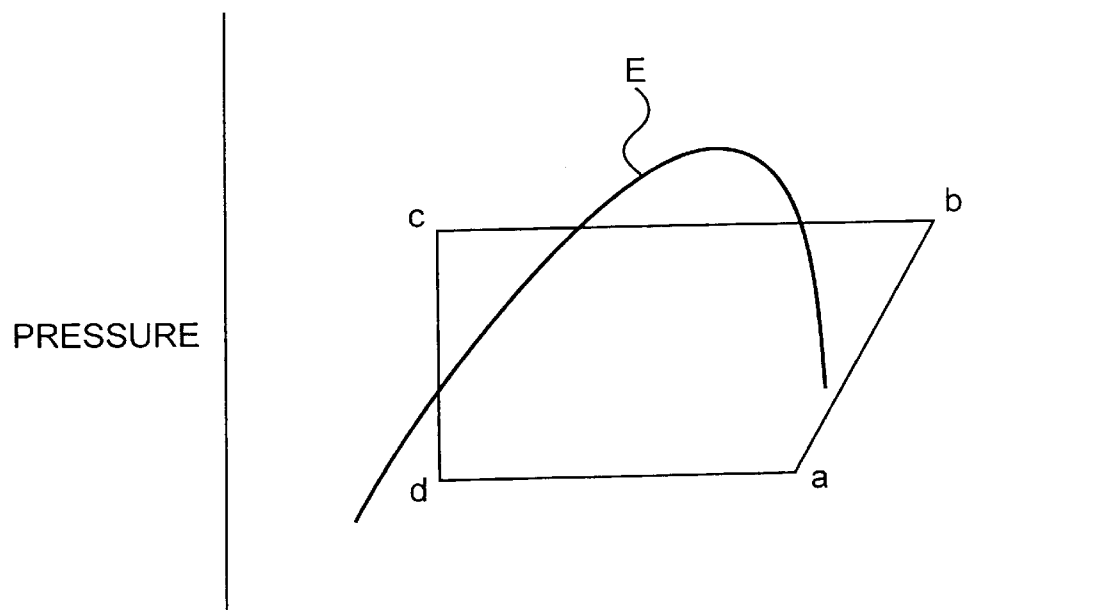
FIG. 2 is a pressure-enthalpy diagram depicting an exemplary "pressure enthalpy dome" characteristic of a refrigerant composition; wherein trapezoid a-b-c-d presents an exemplary refrigeration cycle; and line c-d represents an exemplary isenthalpic expansion.

The trapezoid a-b-c-d of FIG. 2 depicts the thermodynamic operation of the refrigeration system. At a constant pressure, the vaporizing refrigerant in evaporator 9 picks up heat from the surroundings as shown in line d-a. The vapor is compressed in compressor 3, and then heat is exhausted in the constant pressure condensation shown in line b-c. The isenthalpic expansion taking place in the expansion valve 7 is depicted by line c-d.

In the present invention, the temperature of the ternary refrigerant in the liquid phase is measured by temperature measuring device 13 before the expansion. Device 13 preferably is placed immediately adjacent the inlet of the expansion device, although it can be placed at other locations upstream of the expansion device, as long as the state of the measured liquid is substantially the same as that entering the expansion device. The temperature and pressure of the liquid phase and vapor phase after the expansion are measured by second temperature measuring device 15 and pressure measuring device 17. Again, devices 15 and 17 are preferably positioned immediately adjacent the downstream side of the expansion device, although these measurements may be taken in another location provided that the state of the refrigerant is substantially identical to the state of the refrigerant exiting the expansion device.

The operation of the composition calculation concerns the line c-d of FIG. 2. The expansion is isenthalpic only in theory. The calculation according to the present invention assumes an isenthalpic expansion, which the inventor has concluded is sufficiently accurate to provide meaningful information concerning the composition of the ternary refrigerants such as R-407C.

In the method of the present invention, the ternary refrigerant, having a first component, a second component and a third component, enters the expansion device 7 as a liquid. As the pressure is reduced, the refrigerant leaves the liquid phase region on the left side of the "pressure enthalpy dome," line E, and enters the so-called two phase region underneath the dome. At the point where the vertical line c-d crosses line E into the two-phase region, a binary system would be completely described by the temperature, pressure and enthalpy. However, a ternary system has an additional degree of freedom imposed by the additional component. The inventors have concluded that a relatively inexpensive and convenient evaluation can be made of a three component system, where the ratio of two of the components remain relatively constant.

An element of the present invention is the assumption that the ratio of the first component to the second component remains constant. The inventor has concluded that this assumption accurately applies to ternary mixtures such as R-407C. This assumption, together with the assumption of an isenthalpic expansion, permits the calculation of the composition of the ternary refrigerant using as process variable inputs only the upstream temperature and the downstream temperature and pressure.

In a preferred embodiment, the ternary refrigerant consists essentially of difluoromethane (R-32), pentafluoroethane (R-125), and 1,1,1,2 tetrafluoroethane (R-134a), and may be, for example R-407C. In the preferred embodiment, the ratio of R-32 to R-125 is assumed constant. The inventor herein has recognized that these components of this known refrigerant have similar volatilities and form an azeotrope. As a result, the mixtures of these two components may be treated for the purposes herein as essentially one component.

Once the refrigerants like R-407C are selected and the above parameters are sensed and assumptions applied, there are a number of relevant equations of state that may be applied to determine the composition of the refrigerant, particularly the respective weight ratios of its components. As known in the art, computer programs are commercially available for performing the calculations, once these assumptions are applied. The selection of an algorithm for the composition calculation would be readily apparent to persons skilled in the art. By means of example only, the subprogram REFPROP 6, commercially available directly from the National Institute of Standards and Testing (NIST) may be used to converge physical property data to obtain component weight ratios.

The results achieved by the method and system of the invention can be applied to control the refrigeration system to provide optimum results. In addition, the permanent method and systems illustrated generally at FIG. 1 can be used to periodically sample the composition of the refrigerant and determine whether the refrigerant has become fractionated by, for example, leakage. Once the specific composition is known, the refrigerant can be recharged to have the preferred relative weight ratios of components.

In another preferred embodiment, the method and system is used to determine whether a system has fractionated after a leak. For example, the sensors and/or calculator can be designed as a temporary device or system that can be removably attached to the refrigeration system as needed. For example, a refrigeration loop can be designed to include ports upstream and downstream of the expansion device, and sensing devices can be connected to these ports on a temporary basis. When in use, a calculator is operably connected to the process variable outputs of the first and second temperature measuring device 13, 15 and the pressure measuring device 17. The sensors and calculator can be designed as a portable unit. This portable arrangement would enable the use of the method and apparatus of the present invention in an instance where a leak has been detected and an operator wants to know whether and/or the degree to which the ternary refrigerant therein has fractionated, without involving the control apparatus already present on the system. The sensing devices and calculators may be temporarily inserted into ports installed into the refrigeration system.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining the composition of a ternary refrigerant in a refrigeration system having an expansion device, comprising:
   providing a ternary refrigerant, having a first component, a second component, and a third component, in a refrigerant loop including an expansion device;
   measuring an upstream temperature of the ternary refrigerant in the liquid phase upstream of the expansion device;
   expanding the refrigerant in the expansion device so that the ternary refrigerant is present in a vapor phase and a liquid phase downstream of the expansion device;
   measuring a downstream temperature and a downstream pressure of the ternary refrigerant downstream of the expansion device; and
   calculating the composition of the ternary refrigerant with a thermodynamic equation of state,
   wherein, the calculating assumes that the enthalpy is a function of temperature alone and a constant ratio of the first component to the second component in the liquid phase upstream of the expansion device and in the liquid and the vapor phase downstream of the expansion device.

2. The method of claim 1, wherein the step of calculating assumes the expanding is isenthalpic.

3. The method of claim 1, wherein the ternary refrigerant consists essentially of difluoromethane, pentafluoroethane, and 1,1,1,2 tetrafluoroethane.

4. The method of claim 3, wherein the step of calculating assumes a constant ratio of difluoromethane (R-32) to pentafluoroethane (R-125).

5. The method of claim 1, wherein the ternary refrigerant is R-407C.

6. The method of claim 5, wherein the step of calculating assumes a constant ratio of difluoromethane to pentafluoroethane.

7. The method of claim 1, wherein the step of calculating is performed after a leak has been detected, to determine whether the ternary refrigerant has fractionated.

8. The method of claim 1, wherein the step of calculating is performed with a family of tables, charts or graphs.

9. A system for determining the composition of a ternary refrigerant in a refrigeration loop, the system consisting essentially of:
   an expansion device, flow connected in the refrigeration loop, adapted to expand a ternary refrigerant from a liquid phase to a liquid phase and a vapor phase;
   a first temperature sensing device disposed to measure the temperature of the ternary refrigerant in the liquid phase upstream of the expansion device;
   a second temperature measuring device and a pressure sensing device disposed to measure the temperature and pressure, respectively, of the ternary refrigerant in the vapor phase and the liquid phase downstream of the expansion device; and
   a calculator that receives input from the first temperature measuring device, the second temperature measuring device, and the pressure measuring device, and no input from other process variables, and calculates the composition of the ternary refrigerant based on the assumption that enthalpy is a function of temperature alone and that at least two components of the ternary refrigerant maintain a constant ratio of a first component to a second component in the liquid phase upstream of the expansion device and in the liquid and the vapor phase downstream of the expansion device.

* * * * *